US010053701B2

(12) United States Patent
Umemoto

(10) Patent No.: US 10,053,701 B2
(45) Date of Patent: Aug. 21, 2018

(54) PROTEIN HAVING GLYCOALKALOID BIOSYNTHETIC ENZYME ACTIVITY AND GENE ENCODING THE SAME

(71) Applicant: KIRIN HOLDINGS KABUSHIKI KAISHA, Tokyo (JP)

(72) Inventor: Naoyuki Umemoto, Tokyo (JP)

(73) Assignee: KIRIN HOLDINGS KABUSHIKI KAISHA, Tokyo (JP)

(*) Notice: Subject to any disclaimer, the term of this patent is extended or adjusted under 35 U.S.C. 154(b) by 1018 days.

(21) Appl. No.: 14/358,568

(22) PCT Filed: Nov. 19, 2012

(86) PCT No.: PCT/JP2012/079955
§ 371 (c)(1),
(2) Date: May 15, 2014

(87) PCT Pub. No.: WO2013/073699
PCT Pub. Date: May 23, 2013

(65) Prior Publication Data
US 2015/0284733 A1 Oct. 8, 2015

(30) Foreign Application Priority Data
Nov. 17, 2011 (JP) ................ 2011-251927

(51) Int. Cl.
C12N 15/82 (2006.01)
A01H 1/04 (2006.01)
A01H 5/04 (2018.01)
C12N 15/01 (2006.01)
C07K 14/415 (2006.01)
C12N 9/10 (2006.01)
C12Q 1/6895 (2018.01)

(52) U.S. Cl.
CPC .......... *C12N 15/8243* (2013.01); *A01H 1/04* (2013.01); *A01H 5/04* (2013.01); *C07K 14/415* (2013.01); *C12N 9/1096* (2013.01); *C12Q 1/6895* (2013.01); *C12Y 206/01019* (2013.01); *C12Q 2600/156* (2013.01); *C12Y 206/01* (2013.01)

(58) Field of Classification Search
CPC ............ C12N 15/8243; C12N 15/8218; C12N 2310/14; C12N 15/113; C12N 15/8213; A24B 15/243; A01H 1/04; A01H 1/06; A01H 1/00; A01H 5/00; C12Y 206/01; C12Y 206/01019; A61K 36/81
See application file for complete search history.

(56) References Cited

U.S. PATENT DOCUMENTS 7,317,136 B1 * 1/2008 Forster ............... C12N 15/8246 800/278

FOREIGN PATENT DOCUMENTS

WO 2011/025011 A1 3/2011

OTHER PUBLICATIONS

Ludewig, Frank, et al. "Mutants of GABA transaminase (POP2) suppress the severe phenotype of succinic semialdehyde dehydrogenase (ssadh) mutants in *Arabidopsis*." PLoS One 3.10 (2008): e3383.*
Udrişte et al (U.P.B. Sci. Bull., Series B, vol. 76, Iss. 2, 2014).*
McCue, K.F., Allen, P.V., Shepherd, L.V., Blake, A., Maccree, M.M., Rockhold, D.R., Novy, R.G., Stewart, D., Davies, H.V., and Belknap, W.R. (2007). Potato glycosterol rhamnosyltransferase, the terminal step in triose side-chain biosynthesis. Phytochemistry 68: 327-334.*
Clark, Shawn M., et al. "Subcellular localization and expression of multiple tomato γ-aminobutyrate transaminases that utilize both pyruvate and glyoxylate." Journal of experimental botany 60.11 (2009): 3255-3267.*
Ford Y-Y, Ratcliffe RG, Robins RJ (1996) Phytohormone-induced GABA production in transformed root cultures of Datura stramonium: an in vivo 15N-NMR study. J Exp Bot 47: 811-818.*
Friedberg, Iddo. "Automated protein function prediction—the genomic challenge." Briefings in bioinformatics 7.3 (2006): 225-242.*
Evertsz, E. M., et al. "Research Report Hybridization Cross-Reactivity within Homologous Gene Families on Glass cDNA Microarrays." Biotechniques31.5 (2001): 1182-1192.*
Akihiro, Takashi, et al. "Biochemical mechanism on GABA accumulation during fruit development in tomato." Plant and Cell Physiology 49.9 (2008): 1378-1389.*
Akihiro, Takashi, et al. "Biochemical mechanism on GABA accumulation during fruit development in tomato." Plant and Cell Physiology 49.9 (2008): 1378-1389. (Year: 2008).*
Okabe, Yoshihiro, et al. "Tomato Tilling technology: development of a reverse genetics tool for the efficient isolation of mutants from Micro-Tom mutant libraries." Plant and cell physiology 52.11 (2011): 1994-2005. (Year: 2011).*
"Solanum lycopersicum LeGABA-TP2 mRNA for gamma aminobutyrate transaminase isoform2, complete cds.", AB359917, [online], National Center for Biotechnology Information, loaded on Sep. 26, 2008, retrieved on Dec. 11, 2012, Internet, http://www.ncbi.nlm.nih.gov/nuccore/AB359917.
Lisa Arnqvist et al., "Reduction of Cholesterol and Glycoalkaloid levels in Transgenic Potato Plants by Overexpression of Type 1 Sterol Methyltransferase cDNA", Plant Physiol., 2003, pp. 1792-1799, Vo. 131.
Eckart Eich, "Solanaceae and Convolvulaceae: Secondary Metabolites", Springer-Verlag Berlin Heidelberg, 2008, pp. 398-461.
Idit Ginzberg et al., "Potato Steroidal Glycoalkaloids: Biosynthesis and Genetic Manipulation", Potato Research, 2009, pp. 1-15, vol. 52.
Erich Heftmann, "Biogenisis of Steroids in Solanaceae", Phytochemistry, 1983, pp. 1843-1860, vol. 22, No. 9.
"Lycopersicon esculentum gamma-aminobutyrate transaminase subunit precursor isozyme 2 mRNA, complete cds.", AY240230, [online], National Center for Biotechnology Information, loaded on Apr. 11, 2003, retrieved on Dec. 11, 2012, Internet, http://www.ncbi.nlm.nih.gov/nuccore/AY240230.

(Continued)

*Primary Examiner* — Lee A Visone
*Assistant Examiner* — Weihua Fan
(74) *Attorney, Agent, or Firm* — Sughrue Mion, PLLC

(57) ABSTRACT

Provided is DNA of biosynthetic enzyme of glycoalkaloid of solanaceous plant (Solanaceae) such as potato. Provided are a protein having activity on a biosynthetic enzyme of glycoalkaloid of solanaceous plant such as potato, and a method of creating and assaying a novel organism using a gene encoding the protein.

1 Claim, 10 Drawing Sheets

(56) References Cited

OTHER PUBLICATIONS

Kent F. McCue et al., "Metabolic compensation of steroidal glycoalkaloid biosynthesis in transgenic potato tubers: using reverse genetics to confirm the in vivo enzyme function of a steroidal alkaloid galactosyltransferase", Plant Science, 2005, pp. 267-273, vol. 168.

Kent F. McCue et al., "The primary in vivo steroidal alkaloid glucosyltransferase from potato", Phytochemistry, 2006, pp. 1590-1597, Vo. 67.

Kent F. McCue et al., "Potato glycosterol rhamnosyltransferase, the terminal step in triose side-chain biosynthesis", Phytochemistry, 2007, pp. 327-334, vol. 68.

Toshihiro Nohara et al., "The Tomato Saponin, Esculeoside A", Journal of Natural Products, 2010, pp. 1734-1741, vol. 73, No. 10.

International Search Report for PCT/JP2012/079955 dated Dec. 25, 2012.

\* cited by examiner

Fig. 1-1

```
1st Nucleotide Sequence
  File Name      : potato Y
  Sequence Size  : 1377

2nd Nucleotide Sequence
  File Name      : tomato Y
  Sequence Size  : 1374

[96.006% / 1377 bp]

1' ATGGCCAAGA CTACTAATGG ATTTATGGGA CATGATATGT TGGCACCTTT TACTGCGGCA
      ********** *  ****** ********** ********** ******* ** **********
   1" ATGGCCAAGA C---TAATGG ATTTATGGGA CATGATATGT TGGCACCATT TACTGCGGCA

61' TGGATGATTG ATATGGGACC TTTAGTTATA GATAGAGCGG AGGGTTCTTA TGTCTATGAC
      ********** ********** ********** ****  **** ********** **********
  58" TGGATGATTG ATATGGGACC TTTAGTTATA GATAAAGCGG AGGGTTCTTA TGTCTATGAC

121' GTAAATGGAA AGAAGTACCT TGATTCTTTA TCTGGTTTAT GGTGCACAGT GTTAGGGGGA
      ********** ********** ********** ********** *****  ****  ********
 118" GTAAATGGAA AGAAGTACCT TGATTCTTTA TCTGGTTTAT GGTGCTCAGT ATTAGGGGGG

181' AGTGAGCCTC GTCTTATTGA AGCTGCAAAT AAACAACTCA ATAAATTGGC ATTTTACCAT
      ********** ********** ********** ********** ********** *********
 178" AGTGAGCCTC GTCTTATTGA AGCTGCAAAT AAACAACTCA ATAAATTGGC ATTTTACCAC

241' TCATTTTGGA ATCGTTCCAC AAAACCTTCT TTGGATCTTG CAAAGGAGCT CATAAATATG
      ********** *****  **** ***  ****** ********** ********** **********
 238" TCATTTTGGA ATCGTACCAC AAAGCCTTCT TTGGATCTTG CAAAGGAGCT CATAAATATG

301' TTTACTGCAA ATAAGATGGG AAAAGTTTTT TTCACAAATA GTGGATCAGA AGCTAATGAC
      ********** ********** ********** *******  ** ********** **********
 298" TTTACTGCAA ATAAGATGGG AAAAGTTTTT TTCACAAGTA GTGGATCAGA AGCTAATGAC

361' ACTCAGGTGA AGTTGGTGTG GTATTACAAC AATGCCATTG GGAGGCCAAA CAAAAAGAAA
      ********** ********** ********** ********** ********** **********
 358" ACTCAGGTGA AGTTGGTGTG GTATTACAAC AATGCCATTG GGAGGCCAAA CAAAAAGAAA

421' ATTATTTCTC GAAAAAATGC ATACCATGGT TCCACTTATA TGACTGCCGG TCTCTCTGGG
      ********** ********** *********  ********** **********  ***** ***
 418" ATTATTTCTC GAAAAAATGC ATACCATGGC TCCACTTATA TGACTGCCGG TCTCTCCGGG
```

Fig. 1-2

```
 481' CTTCCTGCAC TACATCTAAA ATTTGATTTG CCACCTCCAT ATATTCTTCA CACTGATTGC
      ****  *** ********** ********   ********** ********** **********
 478" CTTCCATCAC TACATCTAAA ATTTGATTTA CCACCTCCAT ATATTCTTCA CACTGATTGC

541' CCTCATTATT GGAACAATCA CTTGCCAGGT GAGACAGAAG AGGAGTACTC AACTAGGTTG
      ********** *****  *** ********** ********** ********** **********
 538" CCTCATTATT GGAACTATCA CTTGCCAGGT GAGACAGAAG AGGAGTACTC AACTAGGTTG

601' GCAAATAATT TGGAAAATCT TATACTCAAA GAGGGTCCTG AAACAGTTGC TGCTTTCATT
      ********** ********** ********** ********** ********** **********
 598" GCAAATAATT TGGAAAATCT TATACTCAAA GAGGGTCCTG AAACAGTTGC TGCTTTCATT

661' GCGGAACCAG TCATGGGAGG AGCAGGTGTC ATAATTCCTC GGAAACCTA TTTTGAGAAG
      ********** ********** ********  **********  *  ** ** *** ** ***
 658" GCGGAACCAG TCATGGGAGG AGCAGGTGTT ATAATTCCTC CAGCTACTTA TTTCGAAAAG

721' ATTCAAGCTG TCTTAAAGAA ATATGACATT CTTTTCATCG CGGATGAGGT GATATGTGGA
      ********** * ******** ********** ********** ****  **** **********
 718" ATTCAAGCTG TTTTAAAGAA ATATGACATT CTTTTCATCG CGGACGAGGT GATATGTGGA

781' TTTGGAAGAC TTGGGACAAT GTTTGGCTGT GATAAGTACA ACATTAAACC TGATCTTGTC
      ********** ********** ********** ********** ******  ** **********
 778" TTTGGAAGAC TTGGGACAAT GTTTGGCTGT GATAAGTACA ACATTAAGCC TGATCTTGTC

841' TCTATAGCAA AGGCTCTTTC TGGTGGATAT ATACCAATTG GTGCTGTGCT TGTAAGCGAA
      ********** ********** ********** ********** ********** ****** ***
 838" TCTATAGCAA AGGCTCTTTC TGGTGGATAT ATACCAATTG GTGCTGTGCT TGTAAGTGAA

901' GAAATTTCCA AGGTCATAAG TGCTCAAAGC AATCAACTTG GTGTTTTTTG CCATGGATTT
      ******** * *********  ******** ********** ********** **********
 898" GAAATTTCTA AGGTCATAAT GTCTCAAAGC AATCAACTTG GTGTTTTTTG CCATGGATTT

961' ACTTATTCTG GACACCCTGT TGCGTGTGCC GTTGCATTGG AAGCACTAAA GATTTATAAG
      ********** ****  **** ********  ********** **********  ** ******
 958" ACTTATTCTG GACATCCTGT TGCGTGTGCG GTTGCATTGG AAGCACTAAA AATCTATAAG

1021' GAAAAAAATA TTACTGAGGT AGTGAACAAA TTATCACCAA AGTTTCAAGA AGGTTTGAAA
      ********** ********** ******  ** ********** ********** **********
1018" GAAAAAAATA TTACTGAGGT AGTGAATAAA TTATCACCAA AGTTTCAAGA AGGTTTGAAA

1081' GCATTTATCG ACAGTCCCAT AATTGGGGAG ATAAGGGGAA CTGGTTTGGT ACTTCTACG
      ******* *  ****** **  ****** *** ********** ******  **  *********
1078" GCATTTATAG ACAGTCCAAT AATTGGAGAG ATAAGGGGAA CTGGTTTAGT ACTTCTACA
```

Fig. 1-3

```
1141' GAGTTTGTTG ATAACAAATC TGCTAATGAT CCTTTTCCAC TAGAATGGGG TGTTGGTACA
      ******* * ********** * ******** **********  ******** **********
1138" GAGTTTGTAG ATAACAAATC TCCTAATGAT CCTTTTCCAC CAGAATGGGG TGTTGGTACA

1201' TATTTTGGAT CACAATGTGA GAAGCATGGG ATGTTGGTAA GTTTTTCTGG TGATCACGTA
      ********** ******* *  ********   ********* * ********** ****** ***
1198" TATTTTGGAT CACAATGTCA AAAGCATGGT ATGTTGGTGA GTTTTTCTGG TGATCATGTA

1261' AATATGGCTC CTCCATTCAC CTTGAGTCTT GAAGAACTTG ATGAGATGAT AAGCATATAT
      ******* * ********** ********** ********** ********** **********
1258" AATATGGCCC CTCCATTCAC CTTGAGTCTT GAAGAACTTG ATGAGATGAT AAGCATATAT

1321' GGGAAAGCAT TGAAGGATAC TGAAAAAAGA GTGGAAGAAC TCAAGTCTCA GAAAAAG
      ********** ********** ********** ********   * ******** *** ***
1318" GGGAAAGCAT TGAAGGATAC TGAAAAAAGA GTGGAAGAAT TGAAGTCTCA GAAGAAG
```

(SEQ ID NO: 2)

(SEQ ID NO: 4)

1: pKT250 transformant #1
2: pKT250 transformant #9
3: pKT250 transformant #11
4: pKT250 transformant #15
5: pKT250 transformant #22
6: pKT250 transformant #8
7: pKT250 transformant #257
8: Non-transformant 1: Solanum circaeifolium FTT14
2: Solanum lignicaule
3: Solanum tuberosum cv. Sassy

Fig. 8

```
              exon 12
Sassy    1 : CAATTGGTGC TGTGCTTGTA AGCGAAGAAA TTTCCAAGGT CATAAGTGCT CAAAGCAATC
             ********** ********** ********** ********** ******  ** **********
FTT13    1 : CAATTGGTGC TGTGCTTGTA AGCGAAGAAA TTTCCAAGGT CATAAGTTCT CAAAGCAATC
             ********** ********** ********** ********** ******  ** **********
FTT14    1 : CAATTGGTGC TGTGCTTGTA AGCGAAGAAA TTTCCAAGGT CATAAGTTCT CAAAGCAATC Sassy   61 : AACTTGGTGA GCATAGTAAT TATCAATATG ATTGAATATT TTTATTAGTA ATTATTATAT
             ********** * ***    *  *****  ******** ******  ******
FTT13   61 : AACTTGGTGA GTATA---TAG TATCAATGTG ATTGAATATT TTTATTAGTA CTTATTATAT
             ********** * ***    *  ******* ** ********** **********  ********
FTT14   61 : AACTTGGTGA GTATA---TAG TATCAATGTG ATTGAATATT TTTATTAGTA CTTATTATAT Sassy  121 : ---------- ---------- ---------- ---------- ----------T TTTTTTGTAT
                                                                    *  *  *
FTT13  119 : ATATATATAT ATATATATAT ATATATATAT ATATATATAT ATATATATGT ATATCATCT-
                                                                   *  *  *****
FTT14  119 : ATATATATAT ATATATATAT ATATATATAT ATATATATAT ATATATATAT ATATATGTAT exon 13
Sassy  132 : -TCATTTATT TATATTTTAG TAATTTTTTC TACAATTAGG TGTTTTTTGC CATGGATTTA
              ** ***    **** * *   *  ******* ********** *********  ****** **
FTT13  178 : ----ATATAT- -ATATATAA- T---TTTTTC TACAATTAGG TGTTTTTTGT CATGGATATA
             **** ***    ***** *     **  ** ** ****** *** ********** ******  **
FTT14  179 : ATCATCTATA TATATATATA TATATTTATC TACAATAAGG TGTTTTTTGT CATGGATATA Sassy  191 : CTTATTCTGG ACACCCTGTT GCGTGTG  (SEQ ID NO: 18)
             ******** ****** *****
FTT13  231 : CTTATTCTGG ACACCCTGTT GCGTGTG  (SEQ ID NO: 19)
             ********** ********** *******
FTT14  239 : CTTATTCTGG ACACCCTGTT GCGTGTG  (SEQ ID NO: 20)
```

The underline indicates exon, and the double underline indicates the region of TA repeats.

SEQUENCE LISTING

```
<160> NUMBER OF SEQ ID NOS: 20

<210> SEQ ID NO 1
<211> LENGTH: 459
<212> TYPE: PRT
<213> ORGANISM: Solanum tuberosum

<400> SEQUENCE: 1

Met Ala Lys Thr Thr Asn Gly Phe Met Gly His Asp Met Leu Ala Pro
1               5                   10                  15

Phe Thr Ala Ala Trp Met Ile Asp Met Gly Pro Leu Val Ile Asp Arg
            20                  25                  30

Ala Glu Gly Ser Tyr Val Tyr Asp Val Asn Gly Lys Lys Tyr Leu Asp
        35                  40                  45

Ser Leu Ser Gly Leu Trp Cys Thr Val Leu Gly Gly Ser Glu Pro Arg
    50                  55                  60

Leu Ile Glu Ala Ala Asn Lys Gln Leu Asn Lys Leu Ala Phe Tyr His
65                  70                  75                  80

Ser Phe Trp Asn Arg Ser Thr Lys Pro Ser Leu Asp Leu Ala Lys Glu
                85                  90                  95

Leu Ile Asn Met Phe Thr Ala Asn Lys Met Gly Lys Val Phe Phe Thr
            100                 105                 110

Asn Ser Gly Ser Glu Ala Asn Asp Thr Gln Val Lys Leu Val Trp Tyr
        115                 120                 125
```

-continued

Tyr Asn Asn Ala Ile Gly Arg Pro Asn Lys Lys Ile Ile Ser Arg
         130                 135                 140

Lys Asn Ala Tyr His Gly Ser Thr Tyr Met Thr Ala Gly Leu Ser Gly
145                 150                 155                 160

Leu Pro Ala Leu His Leu Lys Phe Asp Leu Pro Pro Tyr Ile Leu
             165                 170                 175

His Thr Asp Cys Pro His Tyr Trp Asn Asn His Leu Pro Gly Glu Thr
             180                 185                 190

Glu Glu Glu Tyr Ser Thr Arg Leu Ala Asn Asn Leu Glu Asn Leu Ile
         195                 200                 205

Leu Lys Glu Gly Pro Glu Thr Val Ala Ala Phe Ile Ala Glu Pro Val
210                 215                 220

Met Gly Gly Ala Gly Val Ile Ile Pro Pro Glu Thr Tyr Phe Glu Lys
225                 230                 235                 240

Ile Gln Ala Val Leu Lys Lys Tyr Asp Ile Leu Phe Ile Ala Asp Glu
             245                 250                 255

Val Ile Cys Gly Phe Gly Arg Leu Gly Thr Met Phe Gly Cys Asp Lys
             260                 265                 270

Tyr Asn Ile Lys Pro Asp Leu Val Ser Ile Ala Lys Ala Leu Ser Gly
         275                 280                 285

Gly Tyr Ile Pro Ile Gly Ala Val Leu Val Ser Glu Glu Ile Ser Lys
290                 295                 300

Val Ile Ser Ala Gln Ser Asn Gln Leu Gly Val Phe Cys His Gly Phe
305                 310                 315                 320

Thr Tyr Ser Gly His Pro Val Ala Cys Ala Val Ala Leu Glu Ala Leu
             325                 330                 335

Lys Ile Tyr Lys Glu Lys Asn Ile Thr Glu Val Val Asn Lys Leu Ser
         340                 345                 350

Pro Lys Phe Gln Glu Gly Leu Lys Ala Phe Ile Asp Ser Pro Ile Ile
         355                 360                 365

Gly Glu Ile Arg Gly Thr Gly Leu Val Leu Ser Thr Glu Phe Val Asp
370                 375                 380

Asn Lys Ser Ala Asn Asp Pro Phe Pro Leu Glu Trp Gly Val Gly Thr
385                 390                 395                 400

Tyr Phe Gly Ser Gln Cys Glu Lys His Gly Met Leu Val Ser Phe Ser
             405                 410                 415

Gly Asp His Val Asn Met Ala Pro Pro Phe Thr Leu Ser Leu Glu Glu
             420                 425                 430

Leu Asp Glu Met Ile Ser Ile Tyr Gly Lys Ala Leu Lys Asp Thr Glu
         435                 440                 445

Lys Arg Val Glu Glu Leu Lys Ser Gln Lys Lys
450                 455

<210> SEQ ID NO 2
<211> LENGTH: 1377
<212> TYPE: DNA
<213> ORGANISM: Solanum tuberosum

<400> SEQUENCE: 2
atggccaaga ctactaatgg atttatggga catgatatgt tggcaccttt tactgcggca    60
tggatgattg atatgggacc tttagttata gatagagcgg agggttctta tgtctatgac   120
gtaaatggaa agaagtacct tgattcttta tctggtttat ggtgcacagt gttaggggga   180
agtgagcctc gtcttattga agctgcaaat aaacaactca ataaattggc attttaccat   240

```
tcattttgga atcgttccac aaaaccttct ttggatcttg caaaggagct cataaatatg    300
tttactgcaa ataagatggg aaaagttttt ttcacaaata gtggatcaga agctaatgac    360
actcaggtga agttggtgtg gtattacaac aatgccattg ggaggccaaa caaaaagaaa    420
attatttctc gaaaaaatgc ataccatggt tccacttata tgactgccgg tctctctggg    480
cttcctgcac tacatctaaa atttgatttg ccacctccat atattcttca cactgattgc    540
cctcattatt ggaacaatca cttgccaggt gagacagaag aggagtactc aactaggttg    600
gcaaataatt tggaaaatct tatactcaaa gagggtcctg aaacagttgc tgctttcatt    660
gcggaaccag tcatggggag agcaggtgtc ataattcctc cggaaaccta ttttgagaag    720
attcaagctg tcttaaagaa atatgacatt cttttcatcg cggatgaggt gatatgtgga    780
tttggaagac ttgggacaat gtttggctgt gataagtaca acattaaacc tgatcttgtc    840
tctatagcaa aggctctttc tggtggatat ataccaattg gtgctgtgct tgtaagcgaa    900
gaaatttcca aggtcataag tgctcaaagc aatcaacttg tgttttttg ccatggattt    960 acttattctg gacaccctgt tgcgtgtgcc gttgcattgg aagcactaaa gatttataag   1020
gaaaaaaata ttactgaggt agtgaacaaa ttataccaca agtttcaaga aggttttgaaa   1080 gcatttatcg acagtcccat aattggggag ataagggaa ctggtttggt actttctacg   1140
gagtttgttg ataacaaatc tgctaatgat ccttttccac tagaatgggg tgttggtaca   1200
tattttggat cacaatgtga aagcatggg atgttggtaa gttttctgg tgatcacgta    1260 aatatggctc ctccattcac cttgagtctt gaagaacttg atgagatgat aagcatatat   1320
gggaaagcat tgaaggatac tgaaaaaaga gtggaagaac tcaagtctca gaaaaag     1377
```

<210> SEQ ID NO 3
<211> LENGTH: 458
<212> TYPE: PRT
<213> ORGANISM: Solanum lycopersicum

<400> SEQUENCE: 3

```
Met Ala Lys Thr Asn Gly Phe Met Gly His Asp Met Leu Ala Pro Phe
1               5                   10                  15

Thr Ala Ala Trp Met Ile Asp Met Gly Pro Leu Val Ile Asp Lys Ala
            20                  25                  30

Glu Gly Ser Tyr Val Tyr Asp Val Asn Gly Lys Lys Tyr Leu Asp Ser
        35                  40                  45

Leu Ser Gly Leu Trp Cys Ser Val Leu Gly Gly Ser Glu Pro Arg Leu
    50                  55                  60

Ile Glu Ala Ala Asn Lys Gln Leu Asn Lys Leu Ala Phe Tyr His Ser
65                  70                  75                  80

Phe Trp Asn Arg Thr Thr Lys Pro Ser Leu Asp Leu Ala Lys Glu Leu
                85                  90                  95

Ile Asn Met Phe Thr Ala Asn Lys Met Gly Lys Val Phe Phe Thr Ser
            100                 105                 110

Ser Gly Ser Glu Ala Asn Asp Thr Gln Val Lys Leu Val Trp Tyr Tyr
        115                 120                 125

Asn Asn Ala Ile Gly Arg Pro Asn Lys Lys Ile Ile Ser Arg Lys
    130                 135                 140

Asn Ala Tyr His Gly Ser Thr Tyr Met Thr Ala Gly Leu Ser Gly Leu
145                 150                 155                 160

Pro Ser Leu His Leu Lys Phe Asp Leu Pro Pro Tyr Ile Leu His
                165                 170                 175
```

Thr Asp Cys Pro His Tyr Trp Asn Tyr His Leu Pro Gly Glu Thr Glu
            180                 185                 190

Glu Glu Tyr Ser Thr Arg Leu Ala Asn Asn Leu Glu Asn Leu Ile Leu
        195                 200                 205

Lys Glu Gly Pro Glu Thr Val Ala Ala Phe Ile Ala Glu Pro Val Met
210                 215                 220

Gly Gly Ala Gly Val Ile Ile Pro Pro Ala Thr Tyr Phe Glu Lys Ile
225                 230                 235                 240

Gln Ala Val Leu Lys Lys Tyr Asp Ile Leu Phe Ile Ala Asp Glu Val
                245                 250                 255

Ile Cys Gly Phe Gly Arg Leu Gly Thr Met Phe Gly Cys Asp Lys Tyr
            260                 265                 270

Asn Ile Lys Pro Asp Leu Val Ser Ile Ala Lys Ala Leu Ser Gly Gly
        275                 280                 285

Tyr Ile Pro Ile Gly Ala Val Leu Val Ser Glu Glu Ile Ser Lys Val
290                 295                 300

Ile Met Ser Gln Ser Asn Gln Leu Gly Val Phe Cys His Gly Phe Thr
305                 310                 315                 320

Tyr Ser Gly His Pro Val Ala Cys Ala Val Ala Leu Glu Ala Leu Lys
                325                 330                 335

Ile Tyr Lys Glu Lys Asn Ile Thr Glu Val Val Asn Lys Leu Ser Pro
            340                 345                 350

Lys Phe Gln Glu Gly Leu Lys Ala Phe Ile Asp Ser Pro Ile Ile Gly
        355                 360                 365

Glu Ile Arg Gly Thr Gly Leu Val Leu Ser Thr Glu Phe Val Asp Asn
370                 375                 380

Lys Ser Pro Asn Asp Pro Phe Pro Pro Glu Trp Gly Val Gly Thr Tyr
385                 390                 395                 400

Phe Gly Ser Gln Cys Gln Lys His Gly Met Leu Val Ser Phe Ser Gly
                405                 410                 415

Asp His Val Asn Met Ala Pro Pro Phe Thr Leu Ser Leu Glu Glu Leu
            420                 425                 430

Asp Glu Met Ile Ser Ile Tyr Gly Lys Ala Leu Lys Asp Thr Glu Lys
        435                 440                 445

Arg Val Glu Glu Leu Lys Ser Gln Lys Lys
    450                 455

<210> SEQ ID NO 4
<211> LENGTH: 1374
<212> TYPE: DNA
<213> ORGANISM: Solanum lycopersicum

<400> SEQUENCE: 4
atggccaaga ctaatggatt tatgggacat gatatgttgg caccatttac tgcggcatgg      60
atgattgata tgggaccttt agttatagat aaagcggagg ttcttatgt ctatgacgta      120 aatgaaaga agtaccttga ttctttatct ggtttatggt gctcagtatt agggggagt      180 gagcctcgtc ttattgaagc tgcaaataaa caactcaata aattggcatt ttaccactca      240
ttttggaatc gtaccacaaa gccttctttg gatcttgcaa aggagctcat aaatatgttt      300
actgcaaata agatgggaaa agtttttttc acaagtagtg gatcagaagc taatgacact      360
caggtgaagt tggtgtggta ttacaacaat gccattggga ggccaaacaa aagaaaatt      420 atttctcgaa aaaatgcata ccatggctcc acttatatga ctgccggtct ctccgggctt      480

```
ccatcactac atctaaaatt tgatttacca cctccatata ttcttcacac tgattgccct      540
cattattgga actatcactt gccaggtgag acagaagagg agtactcaac taggttggca      600
aataatttgg aaaatcttat actcaaagag ggtcctgaaa cagttgctgc tttcattgcg      660
gaaccagtca tgggaggagc aggtgttata attcctccag ctacttattt cgaaaagatt      720
caagctgttt taaagaaata tgacattctt ttcatcgcgg acgaggtgat atgtggattt      780
ggaagacttg ggacaatgtt tggctgtgat aagtacaaca ttaagcctga tcttgtctct      840
atagcaaagg ctctttctgg tggatatata ccaattggtg ctgtgcttgt aagtgaagaa      900
atttctaagg tcataatgtc tcaaagcaat caacttggtg ttttttgcca tggatttact      960
tattctggac atcctgttgc gtgtgcggtt gcattggaag cactaaaaat ctataaggaa     1020
aaaaatatta ctgaggtagt gaataaaatta tcaccaaagt ttcaagaagg tttgaaagca     1080
tttatagaca gtccaataat tggagagata aggggaactg gtttagtact ttctacagag     1140
tttgtagata acaaatctcc taatgatcct tttccaccag aatggggtgt tggtacatat     1200
tttggatcac aatgtcaaaa gcatggtatg ttggtgagtt tttctggtga tcatgtaaat     1260
atggcccctc cattcacctt gagtcttgaa gaacttgatg agatgataag catatatggg     1320
aaagcattga aggatactga aaaaagagtg gaagaattga agtctcagaa gaag          1374
```

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 5
caccatggcc aagactacta atggattt                                         28

<210> SEQ ID NO 6
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 6
ccatcaagtt tttgtccatg ag                                               22

<210> SEQ ID NO 7
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 7
gagctctaga tatttgattt gccacctcca t                                     31

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 8
ggatccatat gcttacaagc acagcaccaa                                       30

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 9
taaagcacga ggaagcggt                                           19

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 10
gcacaacaga caatcggct                                           19

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 11
tggggtgttg gtacatattt tg                                       22

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
ttcctctttg gctttctcca                                          20

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 13
tcaagaaagc ttgaaggaat g                                        21

<210> SEQ ID NO 14
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 14
ttactttttc tgagacttga gttcttc                                  27

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide primer

```
<400> SEQUENCE: 15
caattggtgc tgtgcttgta a                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 16
ccccattcta gtggaaaagg a                                              21

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 17
cacacgcaac agggtgtcca                                                20

<210> SEQ ID NO 18
<211> LENGTH: 217
<212> TYPE: DNA
<213> ORGANISM: Solanum tuberosum

<400> SEQUENCE: 18
caattggtgc tgtgcttgta agcgaagaaa tttccaaggt cataagtgct caaagcaatc    60
aacttggtga gcatagtaat tatcaatatg attgaatatt tttattagta attattatat   120
tttttttgta ttcatttatt tatattttag taattttttc tacaattagg tgttttttgc   180
catggattta cttattctgg acaccctgtt gcgtgtg                            217

<210> SEQ ID NO 19
<211> LENGTH: 256
<212> TYPE: DNA
<213> ORGANISM: Solanum cirsaeifolium

<400> SEQUENCE: 19
caattggtgc tgtgcttgta agcgaagaaa tttccaaggt cataagttct caaagcaatc    60
aacttggtga gtatatagta tcaatgtgat tgaatatttt tattagtact tattatatat   120
atatatatat atatatatat atatatatat atatatatat atatatgtat atcatctata   180
tatatatata atttttttct acaattaggt gttttttgtc atggatatac ttattctgga   240
caccctgttg cgtgtg                                                   256

<210> SEQ ID NO 20
<211> LENGTH: 265
<212> TYPE: DNA
<213> ORGANISM: Solanum cirsaeifolium

<400> SEQUENCE: 20
caattggtgc tgtgcttgta agcgaagaaa tttccaaggt cataagttct caaagcaatc    60
aacttggtga gtatatagta tcaatgtgat tgaatatttt tattagtact tattatatat   120
```

```
atatatatat atatatatat atatatatat atatatatat atatatatat atatgtatat       180
catctatata tatatatata tatttatcta caataaggtg tttttttgtca tggatatact       240 tattctggac accctgttgc gtgtg                                             265
```

PROTEIN HAVING GLYCOALKALOID BIOSYNTHETIC ENZYME ACTIVITY AND GENE ENCODING THE SAME

CROSS REFERENCE TO RELATED APPLICATIONS

This application is a National Stage of International Application No. PCT/JP2012/079955 filed Nov. 19, 2012, claiming priority based on Japanese Patent Application No. 2011-251927, filed Nov. 17, 2011, the contents of all of which are incorporated herein by reference in their entirety.

TECHNICAL FIELD

The present invention relates to a method of producing a glycoalkaloid compound characteristic in a solanaceous plant such as potato, a glycoalkaloid biosynthetic enzyme, a DNA encoding the glycoalkaloid biosynthetic enzyme, a method of breeding and selecting a novel solanaceous plant such as potato using the DNA, and a solanaceous plant such as potato which does not produce a glycoalkaloid.

BACKGROUND ART

Glycoalkaloids are a group of compounds derived from plants and also referred to as steroidal alkaloids. The structure of glycoalkaloids contains an isoprenoid having a chain with 27 carbon atoms and a nitrogen atom, and it has been reported that 422 species of *Solanum* plants contain glycoalkaloids (Eich, Solanaceae and Convolvulaceae: Secondary Metabolite (2008), Springer, Chapter 7.8). As to a plant other than those belonging to the genus *Solanum* in the family Solanaceae, some plants belonging to the family Liliaceae are also known to contain glycoalkaloids. Among glycoalkaloids, important ones are chaconine and solanine from potatoes (*Solanum tuberosum*), and tomatine from tomatoes (*Solanum lycopersicum*), which belong to the genus *Solanum* in the family Solanaceae.

Potato is the fourth most produced crop in the world following corn, rice, and wheat. However, it is a well-known fact that toxic chaconine and solanine are contained in the bud coming out of the tuber or the aerial part of the plant. Symptoms of poisoning such as abdominal pain, dizziness, and mild disturbance of consciousness are caused by chaconine or solanine. Chaconine and solanine are easily accumulated in the tuber when the tuber is damaged or exposed to solar light, and thus there is a risk of poisoning accident caused by improper management of tuber.

Poisoning accidents caused by these frequently happen, and recently, a poisoning accident of glycoalkaloid occurred at an elementary school in Nara City, Japan on Jul. 16, 2009 (reported by Asahi.com). Potatoes are usually a safe food because they are managed such that the content of glycoalkaloid is maintained at 20 mg/100 g or less by storing the tuber of potato in a dark place etc. However, in consideration of the risk of such a poisoning accident described above, reducing glycoalkaloids in potatoes is a matter of concern to all of the persons who deal with potatoes such as the breeding, production, storage, transportation, sale, and purchase of potatoes, but has not been achieved to date. The reasons are as follows. A wild potato species with no glycoalkaloids has not been found, the biosynthetic pathway of glycoalkaloid is unconfirmed (Eich, Solanaceae and Convolvulaceae: Secondary Metabolite (2008), Springer, FIGS. 7.24A and 7.24B, and Ginzberg et al., Potato Research (2009) 52: 1-15), and the identification of gene involved in the biosynthetic pathway has not proceeded.

Glycoalkaloids exhibit toxicity such as cholinesterase inhibitory activity or membrane disruption effect, but in addition to this, it is known that glycoalkaloids exhibit medicinal effects such as an anti-cancer activity, a liver protective effect, an antispasmodic effect, an immune system promoting effect, an antifungal effect, an antiprotozoal effect, and a shellfish killing agent activity (Eich, Solanaceae and Convolvulaceae: Secondary Metabolite (2008), Springer). It has also been reported that esculeoside A, which is a metabolite of glycoalkaloids in tomato, exhibits various physiological effects (Nohara et al., J. Nat. Prod. (2010) 73: 1734-1741). However, research and development on suppressing the metabolites or efficient production thereof have hardly proceeded since the biosynthetic pathway thereof is not known.

Several enzyme genes catalyzing the transglycosylation process following the aglycone biosynthesis process have been reported (McCue et al., Plant Sci. (2005) 168: 267-273; McCue et al., Phytochemistry (2006) 67: 1590-1597; McCue et al., Phytochemistry (2007) 68: 327-334). However, in McCue et al., Plant Sci. (2005) 168: 267-273, the gene of UDP-galactosyltransferase, which mediates the conversion of solanidine, which is aglycone, to γ solanine, and a strain in which the gene is suppressed have been reported, but the production of chaconine has not been suppressed at all (McCue et al., Plant Sci. (2005) 168: 267-273, FIG. 2). In McCue et al., Plant Sci. (2005) 168: 267-273, the gene of UDP-glucosyltransferase, which mediates the conversion of solanidine to 7 chaconine, and a strain in which the gene is suppressed have been reported, but the production of either of chaconine and solanine is hardly suppressed (McCue et al., Phytochemistry (2006) 67: 1590-1597, FIG. 5). In McCue et al., Phytochemistry (2007) 68: 327-334, the gene of rhamnosyl transferase, which mediates the conversion of β chaconine to α chaconine and β solanine to α solanine, has been reported, but the β-form and γ-form are increased by the suppression of the gene, although the α-form is decreased. As seen from these, by the suppression of the transglycosylation process, the molecular species of glycoalkaloids can be changed but it is very difficult to control the total amount of glycoalkaloids. Recently, an enzyme gene, which catalyzes the oxidative pathway involved in the biosynthetic pathway of glycoalkaloids, has been reported (WO 2011/025011). However, the specific enzyme reaction has remained unclear.

There is a report of an attempt to decrease in glycoalkaloids by overexpressing biosynthetic genes of plant sterols or plant hormones (Arnqvist et al., Plant Physiol. (2003) 131: 1792-1799). However, the amount of glycoalkaloids can only be reduced to about half at most, and thus an effective means has not been provided in modifying the pathway (Arnqvist et al., Plant Physiol. (2003) 131: 1792-1799, FIG. 5).

Glycoalkaloids is characterized by containing a nitrogen molecule. Research on this biosynthesis is poor. In Heftmann, Phytochemistry (1983) 22: 1843-1860, a review, it is reported that the hydroxyl group at the terminal position 26 is simply replaced with an amino group, and the donor thereof is glycine or alanine in potato of Solanaceae.

SUMMARY OF INVENTION

Technical Problem

An object of the present invention is to provide a method of producing a glycoalkaloid compound characteristic in a solanaceous plant such as potato, a glycoalkaloid biosynthetic enzyme, a DNA encoding the glycoalkaloid biosynthetic enzyme, a method of breeding and selecting a novel solanaceous plant such as potato using the DNA, and a solanaceous plant such as potato which does not produce a glycoalkaloid.

Solution to Problem

The inventor have conducted intensive investigations in order to solve the problems described above. The inventor have noted that nitrogen molecules are contained in glycoalkaloids. Although this biosynthetic process is largely unknown, the candidate genes were found out in silico, and expressed in a form causing RNAi using a part thereof, thereby suppressing the expression of endogenous candidate genes. As a result, potato having a significantly reduced content of glycoalkaloid was successfully obtained among the transformants, and a glycoalkaloid biosynthetic enzyme gene was successfully identified. In addition, the inventor have demonstrated that a solanaceous plant such as potato, which does not contain glycoalkaloids, is obtained by selecting a plant in which expression of the gene is suppressed. Moreover, it is also demonstrated that the production of a novel glycoalkaloid compound is possible by expressing the gene, the analysis of the polymorphism is possible by comparing the genomic sequence of the gene in various solanaceous plants such as potato, and newly bred solanaceous plants, such as potato, can be systematically provided, thereby completing the invention. In the same manner, a tomato having a reduced content of glycoalkaloid have been successfully produced by suppressing the endogenous gene in tomato as well.

In other words, the present invention includes the following inventions.

[1] A protein of the following (a) or (b):
(a) a protein consisting of an amino acid sequence set forth in SEQ ID NO: 1; and
(b) a protein consisting of an amino acid sequence wherein one or several amino acids in an amino acid sequence set forth in SEQ ID NO: 1 are deleted, substituted, inserted, or added, and having glycoalkaloid biosynthetic enzyme activity.

[2] A gene consisting of any DNA of the following (c) to (f):
(c) a DNA consisting of a nucleotide sequence set forth in SEQ ID NO: 2;
(d) a DNA hybridizing with a DNA consisting of a nucleotide sequence complementary to a DNA consisting of a nucleotide sequence set forth in SEQ ID NO: 2 under a stringent condition, and encoding a protein having glycoalkaloid biosynthetic enzyme activity;
(e) a DNA consisting of a nucleotide sequence having a sequence identity of 80% or more with a nucleotide sequence set forth in SEQ ID NO: 2, and encoding a protein having glycoalkaloid biosynthetic enzyme activity; and
(f) a DNA consisting of a degenerate isomer of a nucleotide sequence set forth in SEQ ID NO: 2.

[3] A protein of the following (g) or (h):
(g) a protein consisting of an amino acid sequence set forth in SEQ ID NO: 3; and
(h) a protein consisting of an amino acid sequence wherein one or several amino acids in an amino acid sequence set forth in SEQ ID NO: 3 are deleted, substituted, inserted, or added, and having glycoalkaloid biosynthetic enzyme activity.

[4] A gene consisting of any DNA of the following (i) to (l):
(i) a DNA consisting of a nucleotide sequence set forth in SEQ ID NO: 4;
(j) a DNA hybridizing with a DNA consisting of a nucleotide sequence complementary to a DNA consisting of a nucleotide sequence set forth in SEQ ID NO: 4 under a stringent condition, and encoding a protein having glycoalkaloid biosynthetic enzyme activity;
(k) a DNA consisting of a nucleotide sequence having a homology of 80% or more with a nucleotide sequence set forth in SEQ ID NO: 4, and encoding a protein having glycoalkaloid biosynthetic enzyme activity; and
(l) a DNA consisting of a degenerate isomer of a nucleotide sequence set forth in SEQ ID NO: 4.

[5] A recombinant vector containing the gene according to [2] or [4].

[6] A transformant into which the recombinant vector according to [5] is introduced.

[7] The transformant according to [6], wherein the transformant is a plant.

[8] A method of detecting the presence of a mutation and/or a polymorphism of a gene encoding a glycoalkaloid biosynthetic enzyme in a plant, comprising the steps of:
(i) isolating a nucleic acid, the nucleic acid being genomic DNA or RNA from a plant;
(ii) reverse-transcribing the nucleic acid to synthesize cDNA if the nucleic acid of (i) is RNA,
(iii) amplifying a gene fragment containing at least a part of a nucleotide sequence set forth in SEQ ID NO: 2 or SEQ ID NO: 4 from the DNA obtained in step (i) or (ii); and
(iv) determining the presence of a mutation and/or a polymorphism in the DNA.

[9] The method according to [8], wherein the plant is a solanaceous plant.

[10] A method of detecting a mutation and/or a polymorphism of a gene encoding a glycoalkaloid biosynthetic enzyme by the method according to [8] or [9] and selecting a plant having a mutation and/or a polymorphism.

[11] A plant having a mutation and/or a polymorphism in a gene encoding a glycoalkaloid biosynthetic enzyme, wherein the plant is selected by the method according to [10].

[12] The plant according to [11], which is a solanaceous plant such as potato.

[13] The method of selecting a plant according to [8] or [9], wherein a plant having an altered ability to express a gene encoding a glycoalkaloid biosynthetic enzyme or an altered activity of a glycoalkaloid biosynthetic enzyme encoded with respect to an existing variety.

[14] A plant having an altered ability to express a gene encoding a glycoalkaloid biosynthetic enzyme with respect to an existing variety or an altered activity of a glycoalkaloid biosynthetic enzyme with respect to an existing variety, wherein the plant is selected by the method according to [13].

[15] The plant according to [14], wherein the plant is a solanaceous plant such as potato.

[16] A method of producing a cultivar having a reduced risk of accumulation of glycoalkaloids by screening progeny obtained by crossing a plant suppressed in expression of glycoalkaloid biosynthetic enzyme gene encoded in a DNA sequence set forth in SEQ ID NO: 2 or SEQ ID NO: 4 or a DNA sequence hybridizing with a complementary sequence to the DNA sequence under a stringent condition, or a plant decreased in activity of the enzyme as a mother plant.

[17] The method according to [16], wherein the mother plant is a plant obtained by artificially modifying an aminotransferase gene involved in glycoalkaloid biosynthesis by a mutation treatment, or progeny thereof.

[18] The method according to [16], wherein the mother plant is a plant obtained by screening a wild type strain, or progeny thereof.

[19] The method according to [18], wherein the mother plant is a plant comprising an insertion sequence in an intron of an aminotransferase gene.

[20] The method according to any one of [16] to [19], comprising detecting a mutation of aminotransferase gene involved in glycoalkaloid biosynthesis by a genetic marker upon selecting the progeny obtained by the crossing.

[21] The method according to [20], wherein the genetic marker is a repeating sequence of 20 times or more of TA inserted in an intron.

[22] The method according to any one of [16] to [21], wherein the plant is a solanaceous plant.

[23] The method according to [22], wherein the cultivar is potato.

[24] A cultivar produced by the method according to any one of [16] to [23].

The present specification includes the contents disclosed in the specification and/or drawings of Japanese Patent Application No. 2011-251927, on which a priority of the present application is based.

Advantageous Effects of Invention

According to the present invention, the expression of activity of a protein having activity on the biosynthesis of a glycoalkaloid compound characteristic in solanaceous plants such as potato, and a gene encoding the protein can be regulated. In other words, a method of creating a plant, in which the activity of the gene is regurated, and a solanaceous plant such as potato which does not produce glycoalkaloids, are provided. The present invension enables breeding a solanaceous plant such as potato, characterized in state of containing aglycoalkaloid compound. A glycoalkaloid compound exhibiting various useful physiological activities can be produced in a large amount and at a low cost by the enzyme of the present invention.

BRIEF DESCRIPTION OF DRAWINGS

FIG. 1-1 illustrates the result of analysis on the homology of a biosynthetic gene Y of potato and tomato by DNA analysis software GENETYX (developed by GENETYX CORPORATION). Significantly high homology is seen in general.

FIG. 1-2 illustrates the result of analysis on the homology of the biosynthetic gene Y of potato and tomato by DNA analysis software GENETYX (developed by GENETYX CORPORATION) (continued from FIG. 1-1).

FIG. 1-3 illustrates the result of analysis on the homology of the biosynthetic gene Y of potato and tomato by DNA analysis software GENETYX (developed by GENETYX CORPORATION) (continued from FIG. 1-2).

FIG. 2 is a diagram illustrating the structure of a vector for the suppression of candidate Y gene. In FIG. 2, the internal structure of the right border (RB) and the left border (LB) of T-DNA of the gene part to be introduced, and the restriction enzyme site are indicated.

FIG. 3 is a graph showing the glycoalkaloid content in vitro stem of potato transformants.

FIG. 8 illustrates the structure of intron 12 of the Y gene genome of a wild species and a cultivated species.

DESCRIPTION OF EMBODIMENTS

Hereinafter, the present invention will be described in detail.

1. Novel Glycoalkaloid Biosynthetic Enzyme

Proteins and enzymes of the present invention are glycoalkaloid biosynthetic enzymes contained in solanaceous plants (Solanaceae) such as potato. Potato (*Solanum tuberosum*), tomato (*Solanum lycopersicum*), eggplant (*Solanum melongena*), capsicum (*Capsium annum*), and the like are included in Solanaceae such as potato. In addition, the enzymes of the present invention are aminotransferases. Glycoalkaloids obtained by the enzymes of the present invention include glycoalkaloids synthesized in a solanaceous plant such as potato, and examples thereof include glycoalkaloids of potato such as chaconine and solanine and glycoalkaloids of tomato such as tomatine.

Preferred examples of steroidal compounds to be used as substrates of the glycoalkaloid biosynthetic enzymes of the present invention include cholesterol compounds in a C-26-oxo form. Examples of the cholesterol compounds include cholesterol, sitosterol, campesterol, stigmasterol, and brassicasterol.

The full-length amino acid sequences of the enzymes of the present invention are set forth in SEQ ID NO: 1 or 3. SEQ ID NO: 1 shows the amino acid sequence of the enzyme derived from potato (*Solanum tuberosum*), and SEQ ID NO: 3 shows the amino acid sequence of the enzyme derived from tomato (*Solanum lycopersicum*). Moreover, the proteins of the present invention encompass proteins having an amino acid sequence substantially identical to the amino acid sequence set forth in SEQ ID NO: 1 or the amino acid sequence set forth in SEQ ID NO: 3, and having glycoalkaloid biosynthetic enzyme activity. Here, examples of the substantially identical amino acid sequence include an amino acid sequence in which one or several (1 to 10, preferably 1 to 7, more preferably 1 to 5, still more preferably 1 to 3, and yet more preferably 1 or 2) amino acids are deleted, substituted, inserted and/or added with respect to the amino acid sequence, or an amino acid sequence having a sequence identity of at least 85% or more, preferably 90% or more, more preferably 95% or more, and particularly preferably 97% or more with the amino acid sequence when calculated using (for example, the default, that is, the initial setting parameter) such as BLAST (Basic Local Alignment Search Tool at the National Center for Biological Information (US)).

The glycoalkaloid biosynthetic enzymes of the present invention include a natural glycoalkaloid biosynthetic enzyme isolated from a plant body and recombinant glycoalkaloid biosynthetic enzymes produced by a genetic engineering technique.

2. Gene Encoding Glycoalkaloid Biosynthetic Enzyme

The genes of the present invention is genes encoding the proteins having the glycoalkaloid biosynthetic enzyme activity described above. The genes of the present invention are referred to as Y gene.

Figure 2:
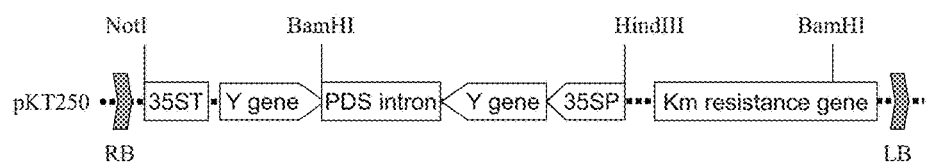
Figure 3:
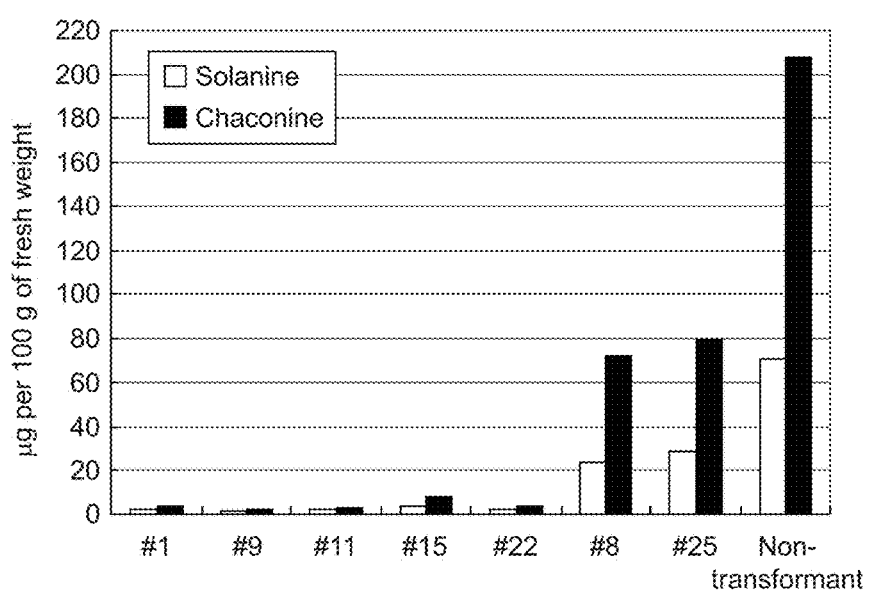

The nucleotide sequences of the DNAs of the genes of the present invention are set forth in SEQ ID NO: 2 or 4. SEQ ID NO: 2 shows the nucleotide sequence of the DNA of the gene derived from potato (*Solanum tuberosum*), and SEQ ID NO: 4 shows the nucleotide sequence of the DNA of the gene derived from tomato (*Solanum lycopersicum*). FIG. 1-1 to FIG. 1-3 illustrate the results of analysis on the homology of the genes of potato and tomato by DNA analysis software GENETYX (developed by GENETYX CORPORATION). Moreover, the DNAs of the genes of the present invention encompass DNAs which hybridize with a DNA having a nucleotide sequence complementary to the nucleotide sequence set forth in SEQ ID NO: 2 or 4 under a stringent condition, DNAs having a sequence identity of at least 85% or more, preferably 90% or more, more preferably 95% or more, and particularly preferably 97% or more with the nucleotide sequence set forth in SEQ ID NO: 2 or 4 as calculated by using (for example, the default, that is, the initialization parameter) such as BLAST (Basic Local Alignment Search Tool at the National Center for Biological Information (US)), or DNAs encoding a protein consisting of an amino acid sequence in which one or several (1 to 10, preferably 1 to 7, more preferably 1 to 5, still more preferably 1 to 3, and yet more preferably 1 or 2) amino acids are deleted, substituted, inserted and/or added with respect to the amino acid sequence of the protein encoded by the DNA, and encoding a protein having glycoalkaloid biosynthetic enzyme activity. Here, the "stringent condition" is, for example, a condition of about "1×SSC, 0.1% SDS, and 37° C.", a more stringent condition is a condition of about "0.5×SSC, 0.1% SDS, and 42° C.", and a still more stringent condition is a condition of about "0.2×SSC, 0.1% SDS, and 65° C.". Moreover, the gene of the present invention includes DNA consisting of a degenerate isomer of the nucleotide sequence set forth in SEQ ID NO: 2 or 4.

3. Recombinant Vector

A vector of the present invention is a recombinant vector in which a DNA of the SEQ ID NO: 2 or the SEQ ID NO: 4 described above is inserted. As a vector, known vectors for *Escherichia coli*, for yeast, for plant cells, for insect cells or the like can be widely used. Components related to the expression or suppression of a gene such as a promoter, a terminator, and/or an enhancer are incorporated into vectors used in the present invention, and a selection marker (for example, a drug resistant gene, an antibiotic resistant gene, and a reporter gene) is included therein if necessary. The components related to the expression or suppression of a gene are preferably incorporated into the recombinant vectors depending on the property thereof and in a manner allowing each component to function. Such an operation can be appropriately carried out by those skilled in the art.

4. Transformant

A transformant of the present invention is a transformant containing the recombinant vector of the present invention. The transformant can be obtained by introducing the recombinant vector, in which a gene encoding an enzyme is inserted, into a host so that the target gene can be expressed. As the host, a host suitable for the vector may be used. Examples thereof include *Escherichia coli*, yeast, plant cells, insect cells (Sf9 or the like), and plant viruses. Preferable examples include *Escherichia coli*, yeast, and plant cells. The introduction method of the recombinant vector is not particularly limited as long as a method is for introducing DNA into a microorganism. Examples thereof include methods using calcium ion [Cohen et al., Proc. Natl. Acad. Sci., USA, 69: 2110 (1972)], electroporation methods, and tri-parental mating methods. In addition, examples of a method of preparing a transgenic plant include methods using a Ti plasmid or an Ri plasmid of a virus or *Agrobacterium* as a vector. Examples of the host plant include monocotyledons such as rice, wheat, and corn, and dicotyledons such as soybean, rapeseed, tomato, and potato. The transgenic plant can be obtained by regenerating a plant cell transformed with a gene of the present invention. The regeneration of a plant from a plant cell can be carried out by a known method.

5. Production of Glycoalkaloid Biosynthetic Enzyme and Production Method of Glycoalkaloid Compound The glycoalkaloid biosynthetic enzymes of the present invention are amino transferases, and can be collected from usual plant bodies. Further, for example, they can be produced by mass production using a microorganism, such as *Escherichia coli* and yeast, or an insect cell expression system which is transformed by a gene of the present invention. Examples of *Escherichia coli* include those disclosed by Clark et al. [2009, J. Exp. Bot. 60: 1743-1757].

Since a protein having a high activity can be expressed using these systems, a glycoalkaloid compound can be produced by adding a substrate of the glycoalkaloid biosynthetic enzyme and a donor of an amino group in a culture solution of *Escherichia coli*. For example, it is possible to produce efficiently a large amount of an aminated cholesterol by administering a cholesterol compound in a C-26-oxo form as a substrate and various amino acids or GABA as a donor of an amino group to the culture solution of transformed *Escherichia coli*. It has been reported (Harada and Misawa Appl. Microbiol Biotechnol. (2008): 1021-31) that yeast has a pathway (mevalonate pathway) to biosynthesize DMAPP in the cytosol, and a precursor or a substrate can be produced by introducing the mevalonate pathway into *Escherichia coli*. It is possible to produce a larger amount of glycoalkaloid compound by combining such methods.

6. Gene Suppression Method

The present invention provides a method of suppressing a glycoalkaloid biosynthetic enzyme gene in a plant. As the suppressing method, it is possible to use a method for suppressing the expression of the gene such as an RNAi method by genetic recombination, an antisense method, a PTGS method using a viral vector, or a method of directly introducing a small RNA or the like. In addition, the suppressing method may be a method of modifying the genome itself such as a ZFN (zinc finger nuclease) method, a TALEN (Tale nuclease) method [Science, 333, 307 (2010], or a Cre-lox P site-specific recombination method. A method utilizing the sequence provided by the present invention as an introduction site for a direct mutation is included in these methods. Alternatively, it is also possible to delete the entire region of glycoalkaloid gene by specifying the sequence of the proximity region from the sequence provided by the present invention, the genomic information, and the like and utilizing the sequence of the proximity region.

7. Selection of Genetic Mutation, Polymorphic Individual, Gene Expression Variation The present invention provides a method for detecting the presence of a glycoalkaloid biosynthetic enzyme gene mutation in a plant, a polymorphism such as a single nucleotide polymorphism (SNP), and a gene expression variation. The mutant individual may be a mutant individual caused by radiation, a chemical treatment, UV irradiation, or spontaneous mutation.

This method includes a step of isolating genomic DNA or RNA from a plant of mutant individuals, various varieties, or growing individuals, and, in the latter case, a step of reverse-transcribing the genomic RNA to synthesize cDNA, a step of amplifying the gene fragment containing the glycoalkaloid biosynthetic enzyme gene from the DNA by using a DNA amplification technique, and a step of determining the presence of a mutation in this DNA. A commercially available kit (for example, DNeasy or RNeasy (manufactured by QIAGEN)) can be used in a method for extracting DNA or RNA. A commercially available kit (for example, SuperScript First-Strand System (manufactured by Invitrogen)) can also be used in a method for the synthesis of cDNA. As the method of amplifying the gene fragment by the use of a DNA amplification technique, a technique such as so-called PCR method or a LAMP method can be used. These mean a group of techniques based on the use of the polymerase in order to achieve the amplification (that is, increasing the copy number) of a specific DNA sequence by a continuous polymerase reaction. This reaction may be used in place of cloning, and the information on the nucleic acid sequence is only needed. Primers complementary to the sequence of the DNA to be amplified are designed in order to perform the amplification of DNA. Next, the primers are generated by automated DNA synthesis. The DNA amplification method is well known in the art, and can be easily performed by those skilled in the art on the basis of the teachings and instructions provided in the present specification. Several PCR methods (and related techniques) are disclosed in, for example, U.S. Pat. No. 4,683,195, U.S. Pat. No. 4,683,202, U.S. Pat. No. 4,800,159, U.S. Pat. No. 4,965,188, and PCR Protocols: A guide to method and applications edited by Innis et al.

In the step of determining the presence of a mutation or a polymorphism in a DNA, a detection method utilizing the homology of a mutant gene and the normal gene, such as a TILLING method (Till et al., 2003, Genome Res 13: 524-530) to detect a mutant using the determination of the nucleotide sequence (Applied Biosystems) or an enzyme that cleaves one side of a mismatched pair may be used. These can be performed by comparing the sequence data obtained from the technique with the gene part of the nucleotide sequence set forth in SEQ ID NO: 2 or SEQ ID NO: 4.

In the step of determining the difference in the mRNA amount, a quantitative PCR such as an RT-PCR method and a real-time PCR method may be adopted with respect to the cDNA using the primer prepared based on the nucleotide sequence set forth in SEQ ID NO: 2 or SEQ ID NO: 4. Thereafter, the difference in the mRNA amount can be determined, for example, by comparing with the amount of cDNA obtained from the variety "Sassy".

In a particularly preferred embodiment, the method of determining the presence of a mutation of glycoalkaloid biosynthetic enzyme gene, which is defined above, is applied to the material obtained from potato (*Solanum tuberosum*) or a related species thereof among solanaceous plants (Solanaceae) (Example 7).

Among the wild species belonging to the potato or related species thereof, there are a large number of wild species whose genotype and phenotype related to the glycoalkaloid biosynthesis are unknown. By screening these wild species, it is possible to select a wild type strain which has a mutation in a biosynthetic gene and in which the accumulation of glycoalkaloid is not detected or is reduced compared to cultivated species, or a strain having a possibility of causing a decrease in the accumulation of glycoalkaloid by crossing (Example 8).

By the above described method of determining the mutation and/or the polymorphism, it is possible to identify, at the nucleotide level, a mutation or a polymorphism in a gene encoding a glycoalkaloid biosynthetic enzyme, further, it is possible to select a plant having a mutation and/or a polymorphism in a gene encoding a glycoalkaloid biosynthetic enzyme. The present invention includes a plant having a mutation or a polymorphism in a gene encoding a glycoalkaloid biosynthetic enzyme obtained in this manner.

In addition, it is possible to determine a mutation or a polymorphism, determine the difference in the amount of mRNA, and select a plant having an altered ability to express a gene encoding a glycoalkaloid biosynthetic enzyme or an altered activity of a glycoalkaloid biosynthetic enzyme.

Here, the altered ability to express a gene encoding a glycoalkaloid biosynthetic enzyme or altered activity of a glycoalkaloid biosynthetic enzyme includes an alteration caused by an artificial mutation, a spontaneous mutation conserved in wild species or the like, or a genetic polymorphism. The alteration in activity means a decrease or an increase in activity. The modification of the activity of glycoalkaloid biosynthetic enzyme includes the decrease or elimination of the inherent normal function of glycoalkaloid biosynthetic enzyme.

Examples of such a mutation of gene include the deletion of the entire gene or a partial gene in a glycoalkaloid biosynthetic gene, the substitution of some nucleotides with other nucleotides, and the insertion of a nucleotide(s). Examples of the insertion of a nucleotide(s) include the insertion of tens to hundreds of contiguous nucleotides in an exon of a glycoalkaloid biosynthetic gene. Examples of the substitution of some nucleotides with other nucleotides include the substitution of conserved 5' splicing sequence in an intron and the insertion of a sequence that results in an abnormal transcription product in an intron, cue to which substitution a normal splicing does not occur. Specifically, for example, a repetitive sequence of 20 times or more, for example, from 20 to 40 times and preferably from 23 to 34 times of TA is inserted in an intron, for example, in the intron between exon 12 and exon 13. The present invention also includes a plant having such a genetic mutation. The present invention also includes the selection of a plant having such a genetic mutation and the use thereof as a mother plant. Moreover, it is possible to produce a cultivar with a reduced risk of the accumulation of glycoalkaloid by screening the progeny obtained by crossing the plant as a mother plant.

Furthermore, a plant having an altered activity of a glycoalkaloid biosynthetic enzyme can also be obtained by modifying the gene encoding the glycoalkaloid biosynthetic enzyme by an artificial mutation treatment. The modification by the mutation of glycoalkaloid biosynthetic enzyme activity of a certain plant means the modification from existing varieties in the species of the plant. The existing varieties include a wild type but not wild species that have occurred naturally, unless the wild species have already been industrially used. The existing varieties mean all varieties that exist when a plant having modified glycoalkaloid biosynthetic enzyme activity is obtained, and includes varieties produced by artificial manipulations such as crossing and genetic manipulation. In addition, in the modification of activity, the activity is not necessarily altered with respect to all of the existing varieties, and if the activity is modified with respect to a specific existing variety, the plant having modified activity is included in the "plants having a modified activity of a glycoalkaloid biosynthetic enzyme". The "plants having a modified activity of a glycoalkaloid biosynthetic enzyme" also include plants having a modified activity without any artificial manipulation but with a mutation in a natural state. It is possible to select a plant having an altered activity in a natural state and establish the plant as a novel variety by the method of the present invention. In addition, when a plant having a modified activity of a glycoalkaloid biosynthetic enzyme is produced by subjecting a certain existing variety to a mutagenesis treatment, the reference to be compared may be the same existing variety or another existing variety other than the variety subjected to the mutagenesis treatment. In addition, crossing a plant obtained by selection from the nature or produced by a mutagenesis treatment and having a mutation or a polymorphism in a gene encoding a glycoalkaloid biosynthetic enzyme may provide a novel plant variety having a fixed mutation in the gene encoding the glycoalkaloid biosynthetic enzyme, and having a modified ability to express the glycoalkaloid biosynthetic enzyme gene or a modified activity of the glycoalkaloid biosynthetic enzyme.

For example, if the plant is potato (Solanum tuberosum), examples of the existing variety include "Cynthia", "Sassy" (sold by Japan Agribio Company), "Sherry", "Danshaku (Baron)", "May Queen", and "Sayaka (Norin registration number: Norin No. 36)". Here, plants having a modified ability to express a gene encoding a glycoalkaloid biosynthetic enzyme or a modified activity of the glycoalkaloid biosynthetic enzyme with respect to an existing variety include plants having an increased or decreased ability to express a gene encoding a glycoalkaloid biosynthetic enzyme with respect to an existing variety and further include plants having increased or decreased activity of a glycoalkaloid biosynthetic enzyme with respect to an existing variety. The present invention includes such a plant having a modified ability to express a gene encoding a glycoalkaloid biosynthetic enzyme or a modified activity of a glycoalkaloid biosynthetic enzyme with respect to an existing variety, as well.

Particularly, plants having a decreased activity of a toxic glycoalkaloid biosynthetic enzyme are preferable. Such a plant synthesizes a low amount of the glycoalkaloid biosynthetic enzyme or cannot synthesize the glycoalkaloid biosynthetic enzyme, and has a low content of the glycoalkaloid biosynthetic enzyme or lacks the glycoalkaloid synthetic enzyme, or has a low or no activity of the glycoalkaloid synthetic enzyme. As a result, the plant has a low content of glycoalkaloids or lack glycoalkaloids. For example, in the case of potato, glycoalkaloids such as chaconine and solanine are not synthesized, and thus amounts of glycoalkaloids, such as chaconine and solanine, synthesized or present in the tuber of potato are little. In addition, in the case of tomato, glycoalkaloids such as tomatine are not synthesized, and thus amounts of glycoalkaloids, such as tomatine, synthesized or present in the fruit of tomato are little.

In the case of potato, in a plant having a low activity of the glycoalkaloid synthetic enzyme or lacking the activity, glycoalkaloids such as chaconine and solanine are not synthesized in the tuber, or the amount of glycoalkaloids such as chaconine and solanine synthesized in the tuber is less compared to the existing varieties above, and thus the amount of glycoalkaloids such as chaconine and solanine present in the tuber is also little.

A cultivar having a decreased or eliminated accumulation of glycoalkaloid, and having an excellent taste or cultivation characteristics can be produced using a plant having a mutation in a glycoalkaloid biosynthetic gene (a mutant strain obtained by artificially modifying an aminotransferase gene involved in the glycoalkaloid biosynthesis by a mutagenesis treatment, or a wild type strain selected by screening) as a mother plant. In the present invention, a cultivar having a decreased or eliminated accumulation of glycoalkaloid is also referred to as a cultivar with a reduced risk of glycoalkaloid accumulation.

8. Production of Cultivar Having Decreased or Eliminated Accumulation of Glycoalkaloid by Crossing It is possible to produce a cultivar having a decreased or eliminated accumulation of glycoalkaloid using a mutant strain obtained by the above described method or a selected wild type strain as a mother plant. In a case in which a mutant strain obtained from a cultivar is used as a mother plant, it is considered to be advantageous that crossing the mutant strains with each other or crossing the mutant strains having a mutation at different sites of the same target gene in terms of early fixation of mutation. A disorder such as incompatibility according to the classic self-incompatibility and the endosperm balance number (EBN) theory with regard to the mating with potato or a related species of potato is known, but these can be subjected to mating or the treatment equivalent to mating by performing a treatment such as direct pollination to the ovule, ovule culture, implementation of normal and reciprocal crossing, and somatic cell hybridization. For these, it is possible to refer to "Potato Dictionary" (2012) edited by Japan Root and Tuber Crops Development Association Inc. Foundation, Zenkoku Noson Kyoiku Kyokai Co., Ltd., and "Handbook of potato production, improvement, and postharvest management" (2006) edited by Gopal and Paul Khurana p. 77-108 Haworth Press Inc. In a case in which a wild type strain is the introduction source having a gene with a mutation, a gene having a mutation can be introduced by setting the parent of the introduction destination as the cultivated species and performing backcrossing with the parent of the introduction destination while maintaining the taste and the excellent characteristics on the cultivation of the cultivated species. In addition, a genetic marker related to a mutation can be acquired by analyzing the site mutated in the gene at the nucleotide sequence level. Moreover, plural genetic markers positioned in the vicinity of the gene can be acquired, and the selection of the progeny in which mutation is introduced at only desired mutation sites can also be efficiently performed by referring to the genome information such as the potato genome sequence (Nature, 2011; 475: 189-95) reported last year. It is possible to put only the necessary part (gene region) from the introduction source to the introduction destination if detailed markers are acquired not only in the vicinity of the gene but also in the region covering the entire genome. In this case, there is a possibility that the separation between the marker and the trait occurs at a certain probability if there is a genetic distance between the marker and the gene (trait) to introduce, and thus the assay of the trait is essential. However, since the genetic mutation found in the present invention is consistent with the trait, the assay of trait is not required, and a reliable assay of the mated seed can be performed at the time when the seed germinates and the DNA thereof is obtained. The assay technique by these DNA markers can be performed by referring to "Genetic analysis at genome level: MAP and QTL" Ukai Yasuo (2001) University of Tokyo Press, or the like. For example, the presence of the DNA markers can be determined using a polynucleotide such as a primer.

EXAMPLES

Hereinafter, the present invention will be described in more detail with reference to Examples, but the present invention is not limited thereto.

(Example 1) Acquisition of Full-Length Sequence of Glycoalkaloid Biosynthesis Candidate Gene Y mRNA was extracted from the sprout of the potato (*Solanum tuberosum*) variety "Sassy" using RNeasy (manufactured by QIAGEN). Total cDNA was synthesized using SuperScript First-Strand System (manufactured by Invitrogen). Recently, Oyama et al. (Proceedings of the 28th Annual Meeting of the Japanese Society for Plant Cell and Molecular Biology (Sendai) (2010) p. 165) have shown that the introduction of an amino group into glycoalkaloid proceeds via an aldehyde form at position 26. It is expected that the amino transferase is involved in the transfer reaction of the amino group to the aldehyde form, but any similar reaction is not known at all. Hence, the gene pAMT encoding the enzyme catalyzing the vanillylamine from vanillin having a completely different structure in capsicum in the same Solanaceae was set as the reference (Lang et al., Plant J. (2009) 59: 953-961). The unigene registered in the Solanaceae Genome Network (http://solgenomics.net/index.pl) was searched by the NCBI Blast method. As a result, the E value of the indicator of homology was significantly low, and six gene fragments having an identity of amino acid of 80% or more at the time of the alignment could be found (SGN-U268561, SGN-U268558, SGN-U277939, SGN-U268560, SGN-U268559, and SGN-U274756). Among these, attention was given to the gene SGN-U268561 of which many EST clones are isolated in the sprout.

The gene was amplified based on this sequence by a PCR (30 cycles, using PrimeSTAR HS DNA Polymerase manufactured by TAKARA BIO INC.) at an annealing temperature of 55° C. using a primer [U1008: caccATGGCCAAGACTACTAATGGATTT (SEQ ID NO: 5, in this primer, 4 bases (cacc) were artificially added to the 5' terminal in order to clone the gene into the vector.), U1007: CCATCAAGTTTTTGTCCATGAG (SEQ ID NO: 6)]. This was cloned into the pENTRTM/D-TOPO entry vector (manufactured by Invitrogen). The nucleotide sequences of the 8 independent clones thus obtained were determined using ABI310 (manufactured by Applied Biosystems). The sequence obtained in this manner is SEQ ID NO: 1, and the amino acid sequence deduced therefrom is SEQ ID NO: 2. The sequence thus obtained exhibited an identity of 82.4% over the full length with respect to the amino acid sequence of the capsicum pAMT exhibiting different enzyme activity.

Meanwhile, the homologous gene of tomato corresponds to SGN-U570903 in the Solanaceae Genome Network (http://solgenomics.net/index.pl). The part including ORF is set forth in SEQ ID NO: 4, and the amino acid sequence of the enzyme encoded from the cDNA sequence is set forth in SEQ ID NO: 3. The nucleotide sequences of the genes of potato and tomato exhibited a homology of 96.0% when compared to each other. Surprisingly, the gene exhibited an identity of 98.9% with the amino acid sequence (Clark et al., J. Exp. Bot. (2009) 60: 3255-3267, and Akihiro et al., Plant Cell Physiol. (2009) 60: 3255-3267) of the gene reported as gamma-aminobutyrate transaminase subunit precursor isozyme 2 (GABA-T2) of tomato (Table 1), but it is not known that the GABA-T2 is involved in the biosynthesis of glycoalkaloid.

(Example 2) Identification of Genomic Gene of Glycoalkaloid Biosynthesis Candidate Gene Y The genome sequence of the potato gene (Xu et al., Nature (2011) 475: 189-197) has been recently reported. The genome sequence is open to the public in HP (http://potatogenomics.plantbiology.msu.edu/index.html) of the Potato Genome Sequencing Consortium Data Release. It is possible to determine the genomic gene of Y based on this sequence.

Three genomic structures of the genomic sequence of the tomato gene are also listed in the Solanaceae Genome Network as SL1.00sc03540, SL2.31ch12, and SL2.40ch12, and it has been reported that the genomic sequence of the tomato gene includes 16 introns. However, the function thereof is not reported at all in the website.

(Example 3) Construction of Vector for Creating Suppression Transformant of Glycoalkaloid Biosynthesis Candidate Gene Y As a method of suppressing the gene by transformation, the expression (commonly referred to as the RNAi method in plants) of the complementary strand gene fragment in the reverse direction having a structure driven by a strong promoter was used [Chuang and Meyerowitz, Proc. Natl. Acad. Sci. USA., 97, 4985-90 (2000), and Wesley et al., Plant J., 27, 581-90 (2001)]. The gene was amplified with respect to the full-length cDNA obtained in Example 1 by a PCR (30 cycles, using ExTaq DNA Polymerase manufactured by TAKARA BIO INC.) at an annealing temperature of 55° C. using a primer [U895: GAGCTCTAGATATTGATTTGCCACCTCCAT (SEQ ID NO: 7), and U896: GGATCCATATGCTTACAAGCACAGCACCAA (SEQ ID NO: 8)]. This was cloned into the pCR4-TOPO vector (manufactured by Invitrogen) to acquire the gene fragment. The pKT250 vector for plant transformation (FIG. 2) was created by performing the ligating the 35S RNA promoter of cauliflower mosaic virus, the gene fragment in the forward direction, the third intron of phytoene desaturase gene of *Arabidopsis thaliana* (AT4g14210), the gene fragment in the reverse direction, and the 35S RNA terminator of cauliflower mosaic virus in this order based on the binary vector pKT11 (JP Patent Publication (Kokai) No. 2001-161373 A).

(Example 4) Production of Transgenic Plant of Potato

The vector prepared in Example 3 was introduced into *Agrobacterium tumefaciens* GV3110 strain by an electroporation method (Plant Molecular Biology Manual, C2, 1-32 (1994) edited by Gelvin and Schilperoor, Kluwer Academic Publishers). The *Agrobacterium tumefaciens* GV3110 strain containing the vector was subjected to a shake culture at 28° C. for 12 hours in a YEB liquid medium [5 g/l beef extract, 1 g/l yeast extract, 5 g/l peptone, 5 g/l sucrose, and 2 mM magnesium sulfate (pH7.2)] containing kanamycin of 50 ppm. The culture solution of 1.5 ml was centrifuged at 10,000 rpm for 3 minutes to harvest, and then the resultant was washed with an LB medium of 1ml to remove kanamycin. The culture solution was further centrifuged at 10,000 rpm for 3 minutes to harvest, and then resuspended in an MS medium [Murashige & Skoog, Physiol. Plant., 15, 473-497

(1962)] containing 3% sucrose of 1.5 ml, thereby obtaining a bacterial solution for infection.

The transformation of potato was carried out according to [Monma (1990) Plant tissue culture 7: 57-63]. The microtuber obtained from "Sassy" (Japan Agribio Company) of a potato variety was sliced into 2 to 3 mm, and used as the material for *Agrobacterium* infection. This was immersed in the bacterial solution of *Agrobacterium* described above, and then placed on a sterilized filter paper to remove the excess *Agrobacterium*. The resultant was placed on an MS medium (including 1 ppm zeatin, 0.1 ppm IAA, 100 µM acetosyringone, and 0.8% agar) in a Petri dish, and cultured at 25° C. for 3 days under the condition of lighting for 16 hours (photon flux density 32 µE/m$^2$s) and without lighting for 8 hours. Subsequently, the resultant was cultured for 1 week in a medium containing carbenicillin of 250 ppm instead of acetosyringone. Thereafter, the resultant was further transferred on a medium containing kanamycin of 50 ppm and was subcultured every 2 weeks. An adventitious bud was formed during this time, and shoot was generated. The stretched shoot was placed on an MS medium which contains carbenicillin of 250 ppm and kanamycin of 100 ppm, but does not contain the growth regulating substance of plant. The rooted shoot was subjected to a PCR (condition: at 95° C. for 5 minutes, 30 cycles (at 95° C. for 30 seconds, at 55° C. for 30 seconds, and at 72° C. for 1 minute), and at 72° C. for 10 minutes) so that the individuals containing the kanamycin resistant gene as a foreign gene were detected in the grown kanamycin resistant plant bodies, whereby it was confirmed that the redifferentiated plant was a transgenic plant. Here, as a primer that specifically amplified the sequence of the kanamycin resistant gene, TAAAGCACGAGGAAGCGGT (SEQ ID NO: 9) and GCACAACAGACAATCGGCT (SEQ ID NO: 10) were used. As described above, 25 lineages of transgenic plant bodies of potato into which the pKT250 vector was introduced were acquired.

(Example 5) Glycoalkaloid Content of Transgenic Plant and Expression Analysis of Candidate Gene Y In vitro stem of 30 individuals obtained in Example 4 was allowed to stretch for one month after subculturing, and 2 to 4 pieces thereof were collected together to be about 100 mg and then the glycoalkaloid content thereof was measured by the following method (JP Patent Publication No. 2011-27429) using liquid chromatography using an alkali resistant reverse phase chromatography column.

In vitro stem of 25 individuals obtained in Example 4 was allowed to stretch for one month after subculturing, and 2 to 4 pieces thereof were collected together to be about 100 mg, and 990 µL of 0.1% formic acid in 80% MeOH aq. and 10 µg/10 µL of brassinolide (manufactured by Brassino Co., Ltd.) as an internal standard were added thereto, and then the resultant was crushed by a mixer mill (1/25 sec, 10 min, and 4° C.). The debris thus obtained was subjected to centrifugation (10,000 rpm, 5 min, and 4° C.) to perform alcohol precipitation. The supernatant of 25 µL was separated from the resultant, a 0.1% formic acid aqueous solution of 475 µL was added thereto, the resultant was filtered through Multiscreen Solvinert (manufactured by Merck Millipore), and then the filtrate was analyzed using LC-MS (LCMS-2010EV manufactured by Shimadzu Corporation, or Alliance e2795 Q-micro manufactured by WATERS). The separation and the analysis were performed under the condition of LC of a column (XBridge™ Shield RP18-5 (φ2.1×150 mm, manufactured by WATERS)) and an isocratic (column oven: 40° C.) mobile phase (A: 10 mM aqueous solution of ammonium bicarbonate (pH 10): B: acetonitrile=40: 60). The quantification was performed using a standard (chaconine and solanine (both of them are manufactured by Sigma-Aldrich Co., LLC.).

Figure 4:
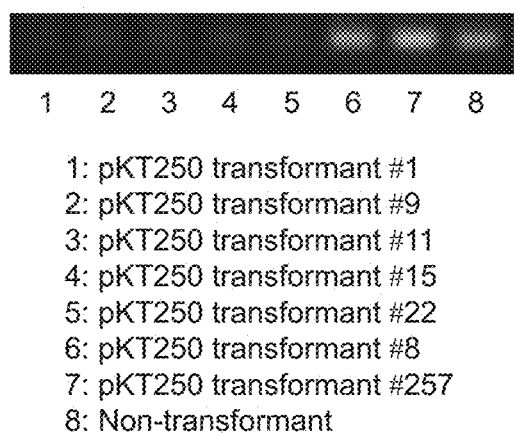
FIG. 4 illustrates the result of a RT-PCR with respect to mRNA extracted from in vitro stem of potato transformants.

It was confirmed that the accumulation of glycoalkaloid was low with favorable reproducibility in five lineages (#1, #9, #11, #15, and #22) by repeating the analysis two times with respect to in vitro stem of 25 individuals thus obtained. About 200 mg of in vitro stem was collected from these five lineages having low glycoalkaloid content, two lineages (#8 and #25) in which the glycoalkaloid content was not low, and one control individual into which a gene was not introduced, respectively, and was ground in liquid nitrogen, thereafter, half of the resultant was subjected to the measurement of glycoalkaloid content and the other half thereof was subjected to the measurement of mRNA. It was reconfirmed that the accumulation of glycoalkaloid in the five lineages having low glycoalkaloid content was significantly low compared to the non-transformant (1 individual) or the two lineages having undecreased glycoalkaloid content (FIG. 3). For each of the lineages, the extraction of entire RNA was performed using RNeasy (manufactured by QIAGEN), and the synthesis of entire cDNA was performed using SuperScript First-Strand System (manufactured by Invitrogen). An RT-PCR was performed (condition: at 95° C. for 5 minutes, 25 cycles (at 95° C. for 30 seconds, at 55° C. for 30 seconds, and at 72° C. for 3 minutes), and at 72° C. for 5 minutes) using a primer [U935: TGGGGTGTTG-GTACATATTTTG (SEQ ID NO: 11), and U1007: TTC-CTCTTTGGCTTTCTCCA (SEQ ID NO: 12)]. As a result, the expression of mRNA of Y gene was significantly low or could not be observed in the five lineages having low glycoalkaloid content (FIG. 4). From this fact, it is verified that the accumulation of glycoalkaloid is extremely reduced by suppressing the expression of a gene of the candidate gene Y, and the candidate gene Y is a gene that encodes a glycoalkaloid biosynthetic enzyme.

(Example 6) Creation of Tuber from Transgenic Plant of Low Glycoalkaloid Content Lineage In vitro plants of three lineages among these five lineages having low glycoalkaloid content were proliferated together with the non-transformants, and three individuals for the respective plants were acclimated to commercially available culture soil for vegetables and cultivated according to a conventional method in a biohazard greenhouse, and the tubers were harvested. Each individual of the three lineages (#9, #11, and #22) showed growth equivalent to the non-transformed plants, and tubers equivalent to those of the non-transformants could be harvested (Table 1).

TABLE 1

| Lineage number | Number of tuber | Standard deviation | Average weight per tuber (g) | Total weight of one plant (g) | Standard deviation |
|---|---|---|---|---|---|
| Nontransformant | 6.3 | 3.6 | 21.6 | 131.9 | 32.7 |
| #9 | 9.0 | 2.1 | 15.2 | 129.9 | 18.5 |
| #11 | 8.7 | 1.0 | 10.8 | 136.0 | 11.5 |
| #22 | 10.3 | 1.5 | 20.8 | 164.2 | 39.5 |

Figure 5:
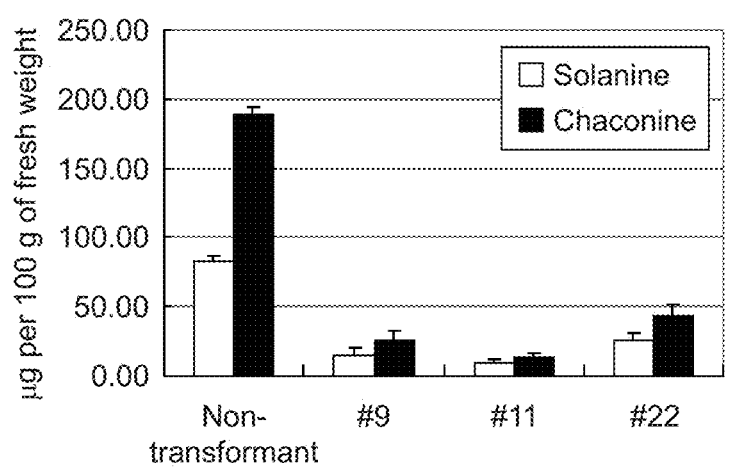
FIG. 5 is a graph illustrating the glycoalkaloid content of the epidermis of tubers of potato transformants. The error bar indicates the standard deviation.

Moreover, the central epidermis of three each tubers of the plants thus harvested were peeled off by about 1 mm, and the glycoalkaloid content thereof was analyzed in the same manner as above. As a result, it was surprisingly confirmed that the glycoalkaloid content in the tubers was significantly low (FIG. 5).

(Example 7) Production of Transgenic Tomato Plant

Figure 6:
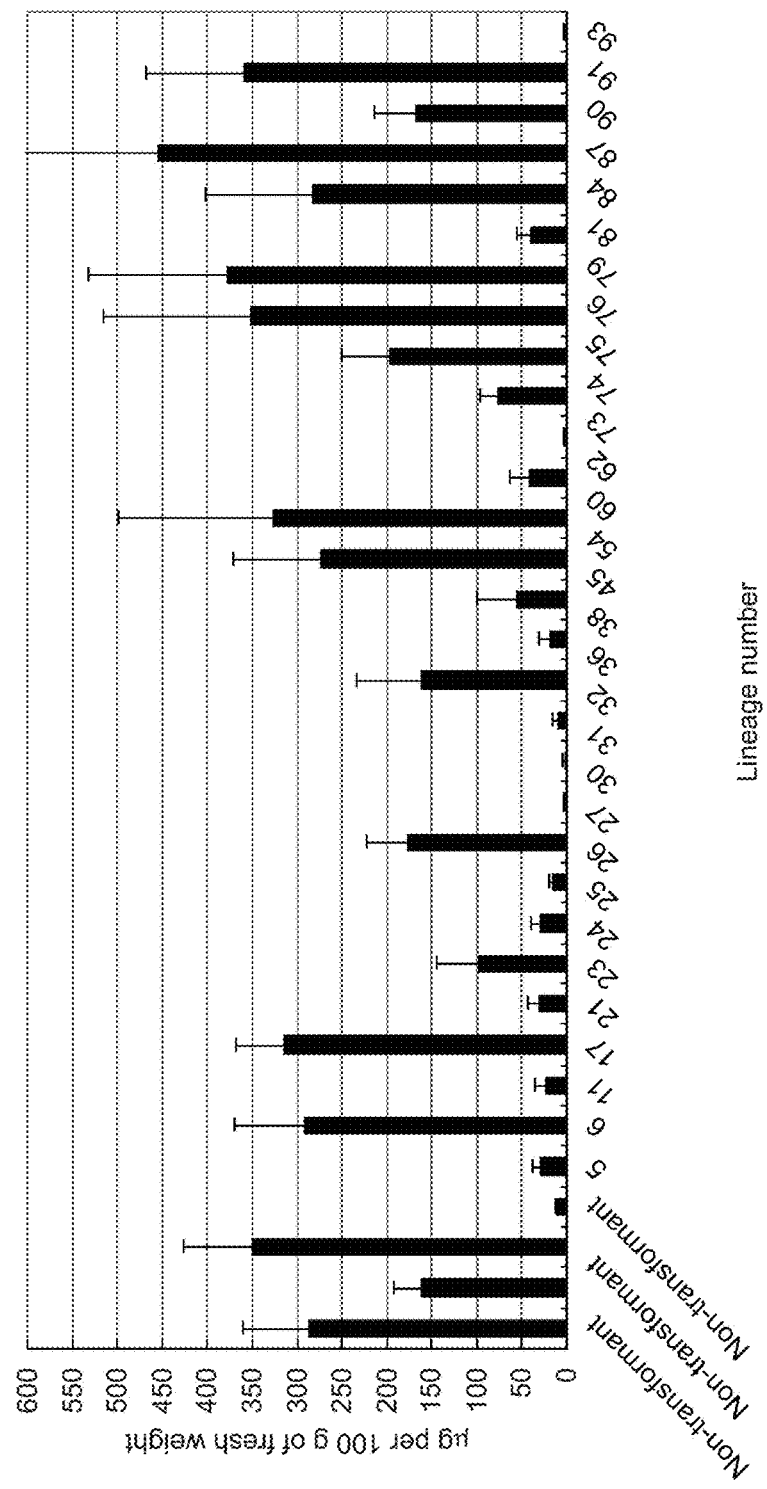
FIG. 6 is a graph illustrating the glycoalkaloid content of young leaves of tomato transformants. The error bar indicates the standard deviation.

The transformation of tomato was carried out according to [Sun et al., (2006) Plant Cell Physiol. 47: 426-431]. An *Agrobacterium tumefaciens* AGL0 strain containing the pKT230 vector prepared in Example 3 was cultured to use as the bacterial solution for infection. The section of 5 mm or smaller of cotyledon of sterile seeded plant of "Microtom" of tomato (*Solanum lycopersicum*) experimental lineage was immersed in the *Agrobacterium* suspension described above and infected for 10 minutes, and then the leaf was placed on a sterilized filter paper to remove the excess *Agrobacterium*. The leaf was placed on a coexistent MS medium (including 1.5 mg/l zeatin, 40 µM acetosyringone, and 0.3% gelrite) [Murashige & Skoog, Physiol. Plant., 15, 473-497 (1962)] in a Petri dish, and the Petri dish was cultured at 25° C. for 3 days in a dark place. The section was subcultured every two weeks in a selected MS medium 1 (including 1.5 mg/l zeatin, 100 mg/l kanamycin, 375 mg/l Augmentin and 0.3% gelrite) at 25° C. under the condition of lighting for 16 hours (photon flux density 32 µE/m²s) and without lighting for 8 hours. An adventitious bud was formed during this time, and shoot was generated. In order to further stretch the shoot, the leaf was transplanted to a selected MS medium 2 (including 1.0 mg/l zeatin, 100 mg/l kanamycin, 375 mg/l Augmentin, and 0.3% gelrite), and the stretched shoot was rooted in a selected MS medium of ½ concentration (including 100 mg/l kanamycin, 375 mg/l Augmentin, and 0.3% gelrite). The shoot was subjected to a PCR by a primer specifically amplifying the sequence of the kanamycin resistant gene described above so that the individuals containing the kanamycin resistant gene as a foreign gene were detected in the grown kanamycin resistant plant bodies, whereby it was confirmed that the redifferentiated plant was a transgenic plant. 30 lineages of transgenic plant of tomato into which the pKT250 vector was introduced were acquired. The 30 lineages thus obtained were acclimated to a greenhouse and cultivated for about one month, and then about 100 mg was weighed from newly developed three young leaves and the glycoalkaloid content (α tomatine content, an α tomatine manufactured by Sigma-Aldrich was used as the standard) thereof was measured by the method of Example 5 in the same manner as potato. Provided that, the proportion of mobile phase A: mobile phase B=60: 40 was used as the analysis condition. The tomatine content of 14 lineages among the 30 lineages was as significantly low as ⅕ or less (<53 µg) of 266 µg per 100 mg of fresh weight that is the average of the control (FIG. 6).

(Example 8) Screening of Plant Having Mutated Glycoalkaloid Biosynthesis Candidate Gene Y In vitro potato plant subcultured in an MS medium [Murashige & Skoog, Physiol. Plant., 15, 473-497 (1962)] containing 3% sucrose, or the like is subjected to a mutation treatment by the quantum beam irradiation (NIRS-HIMAC irradiation device, 0.1 to 3Gy with argon ion beam 500 MeV/nucleon, 0.2 to 3Gy with neon ion beam 400 Mev/nucleon, or 0.5 to 5Gy with carbon ion beam 290 MeV/nucleon). After the mutation treatment, leaves are taken from each of the grown plant bodies, and then the genomic DNA thereof is collected by a conventional method. A PCR is performed using the primer [U1008: caccATGGC-CAAGACTACTAATGGATTT (SEQ ID NO: 5), and U1007: CCATCAAGTTTTTGTCCATGAG (SEQ ID NO: 6)] described above and the genomic DNA as a template to acquire the region including the Y gene, further, the cloning of the region is performed using a kit for gene cloning or the like. The nucleotide sequence of the region cloned is determined, whereby an individual with mutated Y gene can be selected.

Figure 7:
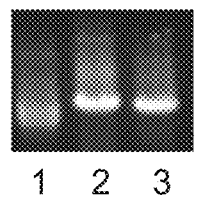
FIG. 7 illustrates the result of electrophoresis of the transcription product of Y gene of a wild species and a cultivated species.

(Example 9) Identification of Plant Having Mutated Glycoalkaloid Biosynthetic Gene Y Plant bodies of five lineages were obtained by germinating a true seed of PI 498120, a wild species obtained from NRSP-6-United States Potato Genebank (http://www.ars-grin.gov/nr6/), belonging to the *Solanum circaeifolium* of a related species of potato (*Solanum tuberosum*). The extraction of the genomic DNA from the both lineages was performed using DNeasy (manufactured by QIAGEN). The extraction of the entire RNA from FTT14 lineage among them was performed using RNeasy (manufactured by QIAGEN), and the synthesis of the entire cDNA was performed using SuperScript First-Strand System (manufactured by Invitrogen). An RT-PCR (condition: at 95° C. for 5 minutes, 30 cycles (at 95° C. for 30 seconds, at 55° C. for 30 seconds, and at 72° C. for 3 minutes), and 72° C. for 5 minutes) was performed (the control was *Solanum lignicale* and the entire cDNA of a variety Sassy) using a primer U1039: TCAAGAAAGCTTGAAGGAATG (SEQ ID NO: 13) and a primer U1040: TTACTTTTTCTGAGACTTGAGTTCTTC (SEQ ID NO: 14) which can amplify the transcription product of Y gene. As a result, it was found that the transcription product was smaller compared to the transcription product of the control and includes a plurality of molecular species in the analysis by agarose electrophoresis (FIG. 7). The amplified transcription product was cloned into the pCR4-TOPO vector (manufactured by Invitrogen), sequenced, and then compared to the sequence of the transcription product of a variety Sassy. As a result, exons 13 and 14 were deleted in clone 1, exons 12, 13, and 14 were deleted in clones 2 and 3, and exons 13, 14, 15, 16, and part of 17 were deleted in clone 4, and thus exon 13 and exon 14 were deleted in common. Hence, a PCR (condition: at 95° C. for 5 minutes, 30 cycles (at 95° C. for 30 seconds, at 55° C. for 30 seconds, and at 72° C. for 3 minutes), and 72° C. for 5 minutes) was performed using the primer U1050: CAAT-TGGTGCTGTGCTTGTAA (SEQ ID NO: 15) of the sequence in exon 12 and the primer U1042: CCCCAT-TCTAGTGGAAAAGGA (SEQ ID NO: 16) of the sequence in exon 15, thereby amplifying the genomic sequence. The amplified genomic sequence was cloned into the pCR4-TOPO vector, sequenced, and then compared to the genome sequence of a variety Sassy. As a result, it was confirmed that there was an abnormal sequence repeating the repetition of TA 20 times or more in intron 12 in the five lineages indicating a transcription product with deleted exon. More specifically, the repetition of 23, 24, 25, 26, 28, 30, 31, and 34 times was observed. From this fact, it was confirmed that the normal splicing did not occur, normal transcription product could not be obtained, and the gene was disrupted. The sequence of intron 12 amplified by the primer U1050 described above and the primer U1051: CACACGCAACA-GGGTGTCCA (SEQ ID NO: 17) of the sequence in exon 13 with respect to the genomic DNA of FTT13 and FTT14 in which an abnormal transcription is carried out, and a variety Sassy in which normal transcription is carried out, is shown in FIG. 8 (SEQ ID NO: 18, 19, and 20 show the sequence of Sassy, FTT13, and FTT14, respectively). From this fact, it is verified that PI 498120 belonging to the *Solanum circaeifolium* is a mutant plant having mutated Y gene.

The glycoalkaloid content of in vitro stem of the plant bodies of the three lineages described above was measured by the method of Example 5. As a result, it was verified that the plant bodies contained only trace amounts of all glycoalkaloids including chaconine, solanine, and tomatine.

The *Solanum circaeifolium* is included in Citcaeifolia (classification of "series" in plant classification), the same series as a normal potato *Solanum tuberosum* according to the literature (C. M Ochoa, 'The Potatoes of South America: Peru, Part I. The Wild Species,' 2004, International Potato Center, Peru). The species belong to EBN1 of different groups in the endosperm balance number (EBN) theory ("Handbook of potato production, improvement, and post-harvest management" (2006) edited by Gopal and Paul Khurana, p. 77-108, Haworth Press Inc.), and it is regarded that the mating is significantly difficult, but a mating example is known (Mattheij et al., (1992) Theor. Appl. Genet. 83: 451-466, and Louwes et al., (1992) Theor. Appl. Genet. 84: 362-370). From these facts, it is verified that the finding of a mutant gene using the sequence of the present gene is easy, and the mutated Y gene that is found from *Solanum circaeifolium* can be used for breeding for industrial applications.

(Example 10) Production of Cultivar by Crossing

The seed lineage FTT14 that is derived from *Solanum circaeifolium* PI 498120 and used in Example 9 is a diploid. The F1 generation is produced by crossing this FTT14 with 97H32-6 (Phumichi et al., Genome (2005) 48: 977-984) of a diploid potato having a self-incompatibility inhibitor gene. It is possible to obtain a potato which has the properties of a diploid potato and does not contain glycoalkaloids in ¼ of the F2 generation acquired by crossing the F1 generation each other. It is possible to obtain a tetraploid potato by subjecting the FTT14 itself or the F2 generation without glycoalkaloids to a doubling treatment using a chemical agent such as colchicine, or the like. It is possible to obtain a novel F1 generation by crossing this tetraploid potato with Hokkaikogane that is a tetraploid and general as a variety. It can be expected that a tetraploid potato without glycoalkaloids is obtained at a proportion of 1/36 of the F2 generation by crossing this F1 generation each other. It is unnecessary to measure the content of glycoalkaloid for the assay, but it is possible to assay the potato by acquiring DNA from the seedling and examining the information of DNA obtained in Example 8, specifically, performing a PCR by a primer U1050 and a primer U1051, and examining the presence or absence of a region of TA repeats in intron 12 by comparing to the amplified fragment of a normal potato.

INDUSTRIAL APPLICABILITY

The method of creating and assaying an organism using the glycoalkaloid biosynthetic enzyme and the gene thereof of the present invention is useful for the development of the production of a glycoalkaloid compound using an organism such as a plant, and the selection of variety of a solanaceous plant such as potato.

All of the publications, patents, and patent applications cited in the present specification shall be incorporated herein by reference in their entirety.

SEQUENCE LISTING FREE TEXT

SEQ ID NOs: 5 to 17 Primers

The invention claimed is:

1. A method of producing a plant belonging to the family Solanaceae having reduced accumulation of glycoalkaloids with respect to an existing variety, said method comprising suppressing the expression of a gene consisting of a DNA selected from the group consisting of (a)-(c) by mutagenesis, RNA interference, or by modifying the plant genome itself:

(a) a DNA consisting of the nucleotide sequence of SEQ ID NO: 2 or SEQ ID NO: 4;
(b) a DNA encoding a protein consisting of the amino acid sequence of SEQ ID NO: 1 or SEQ ID NO: 3; and
(c) a DNA encoding a protein having at least 95% identity with the amino acid sequence of SEQ ID NO: 1 or SEQ ID NO: 3 and having aminotransferase activity;

thereby producing the Solanaceae plant with reduced accumulation of glycoalkaloids.

* * * * *